US00PP12503P2

(12) United States Plant Patent
Hansen

(10) Patent No.: US PP12,503 P2
(45) Date of Patent: Apr. 2, 2002

(54) HOSTA PLANT NAMED 'OLD GLORY'

(75) Inventor: Hans A. Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 0 days.

(21) Appl. No.: 09/454,010

(22) Filed: Dec. 3, 1999

(51) Int. Cl.[7] ..... A01H 5/00
(52) U.S. Cl. ..... Plt./353

(58) Field of Search ..... Plt./353

*Primary Examiner*—Bruce R. Campell
*Assistant Examiner*—Michelle Kizilkaya
(74) *Attorney, Agent, or Firm*—Vidas, Arrett & Steinkraus, P.A.

(57) ABSTRACT

A distinct cultivar of Hosta plant named 'Old Glory', characterized by a unique variegation pattern with relatively wide dark-green margins and light-yellow centers. The new Hosta including clusters of lavender flowers positioned above the foliage.

3 Drawing Sheets

BACKGROUND OF THE INVENTION

The present invention relates to a new and distinct cultivar of Hosta plant, botanically known as Hosta×'Old Glory'.

The new cultivar was discovered by the inventor in Waseca, Minn. United States of America, as a naturally-occurring leaf mutation of the non-patented Hosta hybrid 'Glory' (unpatented), which is a hybrid of Hosta 'August Moon' (unpatented), and was observed in a group of plants of the parent cultivar in 1996.

Asexual propagation of the new cultivar in 1999 at Waseca, Minn., The United States of America, by division and tissue culture has shown that the unique features of this new Hosta plant are stable and reproduced true to type in successive generations of asexual propagation.

BRIEF SUMMARY OF THE INVENTION

The following traits have been repeatedly observed and are determined to be the unique characteristics of 'Old Glory'. These characteristics in combination distinguish the new Hosta as a new and unique cultivar:

1. Medium size cordate leaves with a slightly rippled leaf margin comprising a medium to large sized plant mound;
2. Light yellow leaves maturing to darker yellow with an uneven dark green margin; and
3. Clusters of lavender funnel-shaped flowers are presented above the foliage in mid-summer.

The new Hosta can be compared to its parent cultivar, 'Glory'. In the new Hosta the leaves acquire a variegation pattern wherein the leaves are substantially light yellow with uneven dark green margins, whereas in the parent 'Glory' as well as in the plant 'August Moon' the leaves have a fairly uniform yellow color.

The new Hosta cultivar has not been observed under all possible environmental conditions. The phenotype may vary to some extent with variations in environmental conditions such as temperature and light intensity, without any variance in genotype.

BRIEF DESCRIPTION OF THE PHOTOGRAPHS

The accompanying colored photographs illustrate the overall appearance of the new cultivar, showing the colors as true as is reasonably possible to obtain in colored reproductions of this type.

The first sheet of photographs comprises a top perspective view of a typical plant of the new Hosta.

The second sheet of photographs comprises a top perspective view of a typical plant of the new Hosta wherein the inflorescence including the flowers and peduncles may also be seen.

The third sheet of photographs comprises a close-up view of a typical leaf of the Hosta×'Old Glory'.

Leaf and flower colors in the photographs may appear differently from the actual colors due to light reflectance.

DETAILED DESCRIPTION OF THE INVENTION

In the following description, color references are made to The Royal Horticulture Society Colour Chart except where general terms of ordinary dictionary significance are used. The following observations and measurements describe a three-year old plant, as depicted in the accompanying color photographs, which was grown outdoors in Waseca, Minn., United States of America.

Botanical classification: Hosta×'Old Glory'.
Parentage: Hosta×'Glory'.
Propagation:
*Method.*—By division and tissue culture.
Plant description:
*Plant shape.*—Mounding, dome-shaped, symmetrical.
*Growth habit.*—Initially upright when young, with leaves outwardly arching as they mature.
*Culture.*—Light to medium shade in moist soil.
*Plant type.*—Herbaceous perennial.
*Plant height.*—About 14 inches from soil level to top of leaf plane.
*Plant diameter.*—About 36 inches.
*Vigor and growth rate.*—Moderate to high.
*Disease resistance.*—No known particular resistance or susceptibility to disease known to Hosta observed.
Foliage description:
*Leaf shape.*—Cordate with slight ripple of outer leaf margin.

*Leaf margin.*—Entire.

*Leaf texture.*—Leaves are fairly smooth with the exception of ridges formed by the leaf veins.

*Leaf size.*—Length: About 8.5 inches. Width: About 7.5 inches.

*Venation pattern.*—Campylodrome with 10 pairs of veins.

*Leaf color.*—Centers: Emerge in yellow-green (about 145D) maturing to yellow (11C) by early to mid-summer. Margins: Green (about 131C), margins being ¾ of an inch to 2 inches wide.

Petioles description: In a mature plant petioles may have a length of approximately 25–30 centimeters in and a diameter of about 1 cm. Petiole color is yellow-green.

Flower description:

*Bloom period.*—Mid-summer.

*Fragrance.*—No observed fragrance.

*Flower arrangement.*—Raceme comprised of numerous single flowers having six tepals. Each inflorescence having around 25 flowers, with each flower lasting approximately 1 day.

*Flower shape.*—Funnel-shaped.

*Flower size.*—Approximately 4.5–5 cm.

*Flower color.*—Lavender (85D).

Scape description:

*Number.*—The number of scapes per plant is dependent on the maturity of the plant. Each mature eye comprising the clump may produce a flower scape under normal growing conditions. The scape has a color approximately the same as that the leaf interior. The length of the scape may be up to and about 25 inches in a mature plant with a diameter of about 0.5 to 1 cm and having a round shape and smooth texture.

Description of reproductive organs: The reproductive organs comprise six stamens and a compound ovary having three locules. The size of the anther is Approximately 0.5 cm with a color of 11A. The pollen is average in abundance. The stigma is a three lobed stigma of color 155C, and the style has a color of 155A.

Seed development: Has not been observed.

Root development: From transfer to rooting media in tissue culture, rooting takes approximately 4 weeks at about 68 degrees Fahrenheit. After transfer from stage III in tissue culture to planting into soil in a green house, a well rooted plant is produced in approximately 8 weeks with a day time temperature of about 68 degrees Fahrenheit (about 65 degrees Fahrenheit at night) and a soil temperature of about 78 degrees Fahrenheit.

I claim:

1. A new and distinct cultivar of Hosta plant named 'Old Glory', as illustrated and described.

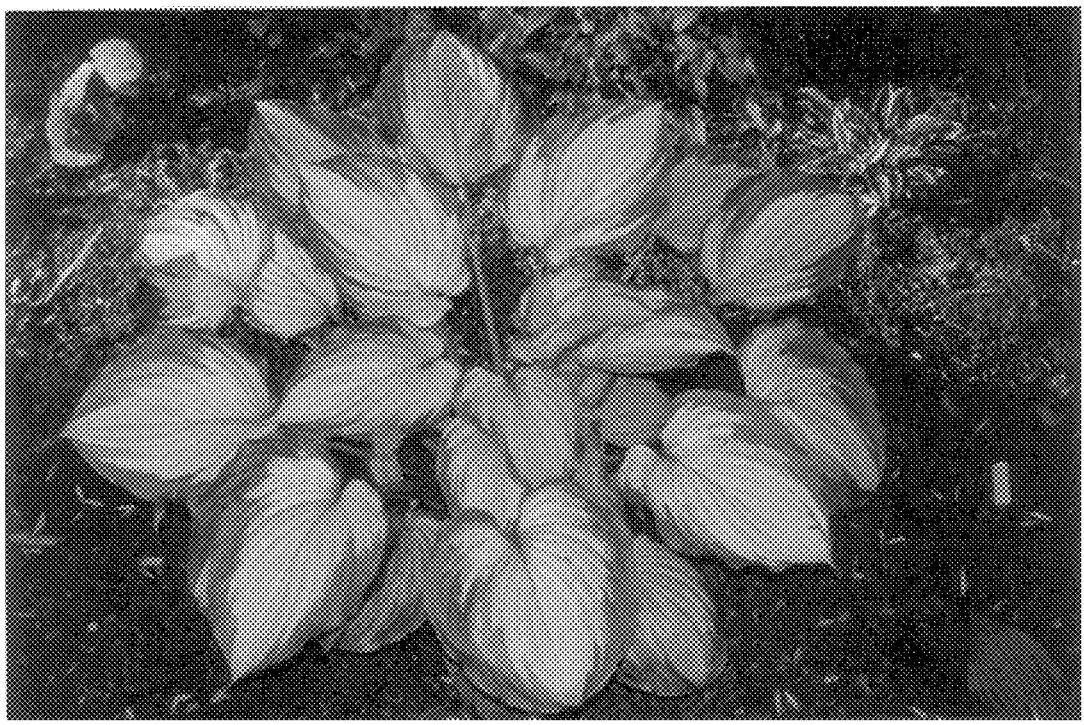

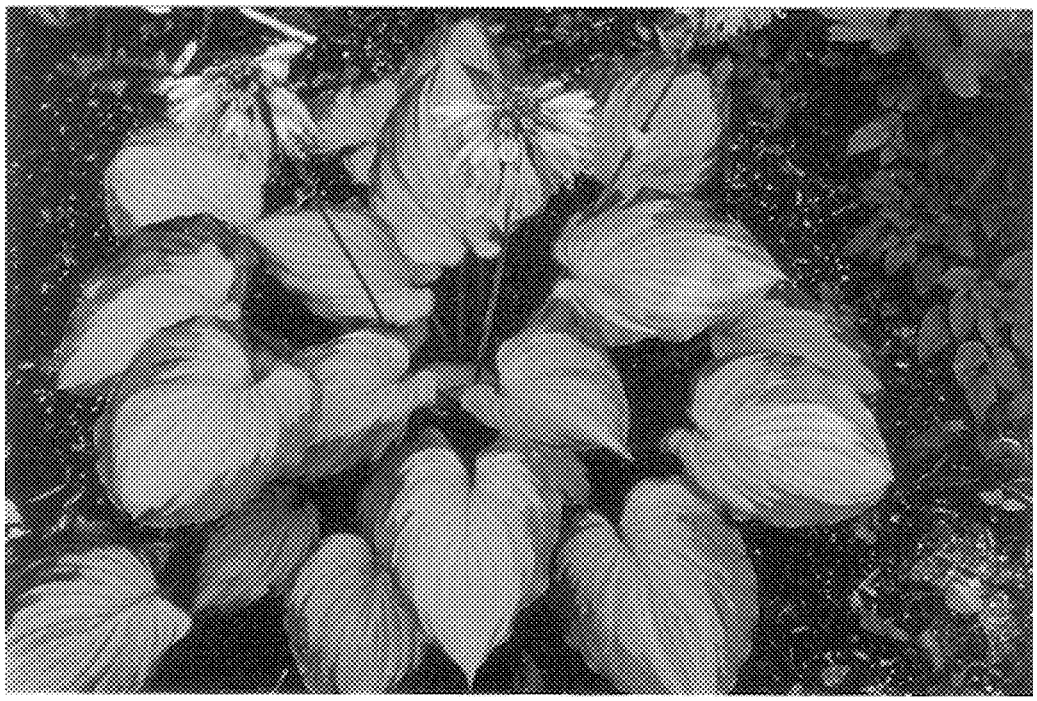

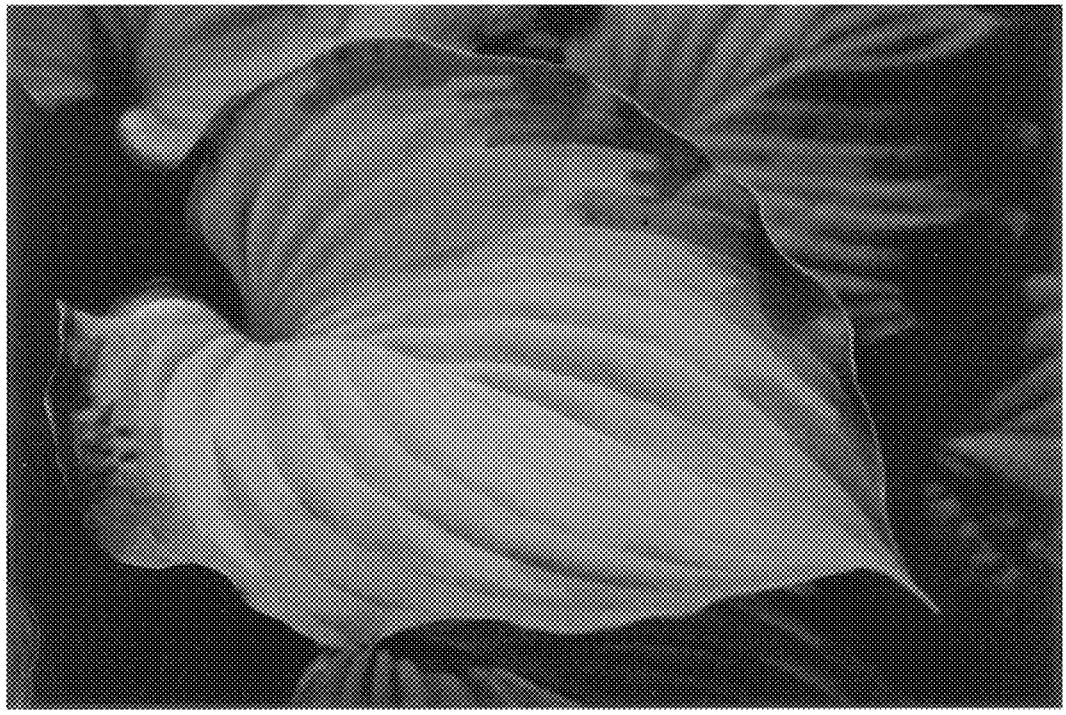

* * * * *